(12) United States Patent
Katoot et al.

(10) Patent No.: US 6,184,030 B1
(45) Date of Patent: *Feb. 6, 2001

(54) BIOLOGICALLY-ACTIVE POLYMERS

(76) Inventors: Mohammad W. Katoot, Roswell, GA (US) 30075; Karen Robbyn Goodan Katoot, administrator, 1080 Laurian Park Dr., Roswell, GA (US) 30075; Ali Maroof Katoot, administrator, 2841 Cory Ct. SW., Apartment 1, Cedar Rapids, IA (US) 52404; Ahmed Maroof Katoot, administrator, Lulworth La., Lawrenceville, GA (US) 30044

(*) Notice: Under 35 U.S.C. 154(b), the term of this patent shall be extended for 0 days.

(21) Appl. No.: 09/023,257

(22) Filed: Feb. 13, 1998

Related U.S. Application Data

(63) Continuation of application No. 08/724,461, filed on Oct. 1, 1996, now abandoned, which is a continuation-in-part of application No. 08/599,888, filed on Feb. 12, 1996, now abandoned.

(60) Provisional application No. 60/004,757, filed on Oct. 2, 1995, and provisional application No. 60/022,825, filed on Jul. 26, 1996.

(51) Int. Cl.[7] ............. C12M 1/34; G01N 33/557; G01N 21/00
(52) U.S. Cl. ............. 435/287.2; 435/7.2; 436/517; 436/518; 436/164; 436/172; 424/48.18; 204/418
(58) Field of Search ............. 435/7.21, 7.1, 435/240.2, 7.8, 287.2, 288.7; 424/78.18, 78.3, 143.1, 159.1, 163.1; 204/403, 418; 436/517, 518, 528, 43, 531, 532, 149, 806, 151, 165, 172

(56) References Cited

U.S. PATENT DOCUMENTS

| | | |
|---|---|---|
| 4,839,017 | 6/1989 | Taniguchi et al. .......... 204/403 |
| 5,035,994 | 7/1991 | Civin ...................... 435/2 |
| 5,202,261 | 4/1993 | Musho et al. ............. 435/288 |
| 5,250,439 | 10/1993 | Musho et al. ............. 435/25 |
| 5,312,762 | 5/1994 | Guiseppi-Elie ............ 436/149 |
| 5,352,574 | 10/1994 | Guiseppi-Elie ............ 435/4 |
| 5,766,934 * | 6/1998 | Guiseppi-Elie ............ 435/287.9 |

FOREIGN PATENT DOCUMENTS

| | | |
|---|---|---|
| 0 193 154 | 9/1986 | (EP). |
| WO 94/20841 | 9/1994 | (WO). |
| WO 94/28418 | 12/1994 | (WO). |
| WO 97/12989 | 4/1997 | (WO). |

OTHER PUBLICATIONS

Sadik, et al., "Pulsed Amperometric Detection of Thaumatin Using Antibody–containing Poly(pyrrole) Electrodes", *The Analyst*, vol. 119, No. 9, pp. 1997–2000, (1994).

Qiu, et al., "Electrochemically Initiated Chain Polymerization of Pyrrole in Aqueous Media", *Journal of Polymer Science–Part A: Polymer Chemistry*, vol. 30, No. 7, pp. 1315–1325, (1992).

Serpa, G., "Biosensor Research Targets Medical Diagnostics", *Medical Device & Diagnostic Industry* pp. 44–54 (1997).

Baxter, "Scientific Products Catalog", Baxter Diagnostics, Inc., Scientific Products Division, pp. 1939–1940 (1991).

Pierce, "ImmunoTechnology Catalog & Handbook", vol. 1, pp. B–12–B–19 (1991).

* cited by examiner

Primary Examiner—Keith D. MacMillan
Assistant Examiner—P. Ponnaluri
(74) Attorney, Agent, or Firm—Jones & Askew, LLP

(57) ABSTRACT

This invention relates to biologically-active polymers that are useful for analyte detection and isolation and delivery of substances. The biologically-active polymers are capable of specifically and reversibly binding to analytes, including molecules and cells. The biologically-active polymers are also capable of releasing substances upon electrical stimulation. The present invention provides compositions comprising biologically-active polymer membranes and methods for making these biologically-active polymer membranes that may be specifically designed to selectively bind cells and specific cell types, to affect cell growth characteristics, and to modulate cellular differentiation. These biologically-active polymer membranes may be controlled electrically to induce controlled cellular differentiation and modulate the cell growth cycle. These biologically-active polymers have many applications in biological and chemical fields.

23 Claims, 3 Drawing Sheets

BIOLOGICALLY-ACTIVE POLYMERS

PRIOR RELATED APPLICATIONS

This application is a continuation of U.S. patent application No. 08/724,461, filed Oct. 1, 1996, now abandoned which claims priority to U.S. provisional patent application Ser. No. 60/004,757 filed on Oct. 2, 1995, and to U.S. provisional patent application Ser. No. 60/022,825 filed on Jul. 26, 1996, and this application is a continuation of application Ser. No. 08/724,461, filed on Oct. 1, 1996, now abandoned, which is a continuation in part of application Ser. No. 08/599,888, filed on Feb. 12, 1996, now abandoned.

TECHNICAL FIELD

This invention relates to biologically-active polymers that are useful for analyte detection and isolation and delivery of substances. More specifically, this invention relates to polymers that are capable of specifically and reversibly binding to analytes, including molecules and cells. The polymers of this invention are also capable of releasing substances upon electrical stimulation. The present invention relates to polymer membranes that act as substrates for cell adhesion, growth and differentiation. The present invention also relates to methods for making these polymer membranes and for specifically making polymer membranes and controlling them so as to have characteristic and specific properties for cell adhesion, growth and differentiation. These polymers have many applications in biological and chemical fields.

BACKGROUND OF THE INVENTION

Analyte Detection

For many years, scientists and physicians have sought rapid, simple and reliable methods for isolating and measuring analytes of all kinds including cells, cell organelles, molecules, and atoms. Most methods of isolating and measuring analytes have involved complicated and expensive analytical equipment such as spectrophotometers, densitometers, gamma and scintillation counters, flow cytometric devices, gas and ion exchange chromatographs, affinity columns, high performance liquid chromatographs and the like. In addition, many of these methods involve the use of various kinds of radiolabels such as $^{125}I$, $^{3}H$, $^{14}C$, $^{32}P$ and others. These isotopes are expensive, require careful disposal and in some cases pose a health threat to laboratory personnel. Non-radioactive methods of analyte detection involve fluorescent, calorimetric, magnetic, and enzyme-linked assay methods among others. All of these methods involve expensive and sophisticated equipment, multiple additions of various reagents, mixing, incubating at different temperatures, and some separation steps, for example centrifugation, and take several hours if not days to complete. Furthermore, these methods do not permit in vivo measurement of an analyte or measurement of multiple analytes in a single system. Usually, a sample must be removed from a patient and subjected to various processing steps before attempting to include the sample in the assay system.

Accordingly what is needed is a rapid, simple, non-isotopic method that does not involve labeling of analytes or other reagents, and minimizes sample manipulation before performing the assay. Furthermore methods are needed that provide a means to measure one or more than one analyte in vivo and in vitro. What is also needed is a system that learns to detect patterns of analyte values associated with the presence of a certain condition or disease.

Substance Delivery

Health care providers such as physicians, nurses, therapists and others, and research scientists have long sought simple reliable, and controlled methods of delivering drugs and other substances to specific locations. Such targeted substance delivery has often been hampered by the typical problems involving substance solubility and stability, the rate and pattern of release of the substance, dilution in the general circulation before reaching the target site, and toxicity of the substance in systems that are not the desired target site.

What is desirable is a system that provides for targeted substance delivery in a controlled fashion. Such a system should be capable of delivering one or more than one substance, of being implanted into a patient, and of being activated by external signals to release substances at specific times and in specific amounts.

Analyte Detection and Substance Delivery System

What is also needed is a system that detects an analyte, analyzes the amount of analyte, and if the amount exceeds or does not meet a certain threshold, sends a signal to another membrane containing a desired substance for release of the substance at a desired location such as into a patient.

Isolation of Cells and Organelles

The human hematopoietic system is populated by cells of several different lineages. These "blood cells" may appear in bone marrow, the thymus, lymphatic tissue(s) and in blood such as umbilical cord blood, and also arterial blood and venous blood obtained centrally or peripherally. Within any specific lineage, there are a number of maturational stages. In most instances, the more immature developmental stages occur within bone marrow while the more mature and final stages of development occur in peripheral blood.

There are two major lineages: The myeloid lineage which matures into red blood cells, granulocytes, monocytes and megakaryocytes; and the lymphoid lineage which matures into B lymphocytes and T lymphocytes. Within each lineage and between each lineage, antigens are expressed differentially on the surface and in the cytoplasm of the cells in a given lineage. The expression of one or more antigens and/or the intensity of expression can be used to distinguish between maturational stages within a lineage and between lineages. Assignment of cell to lineage and to a maturational stage within a cell lineage indicates lineage commitment.

There are cells, however, which are uncommitted to any lineage (i.e., "progenitor" cells) and which, therefore, retain the ability to differentiate into each lineage. These undifferentiated, pluripotent progenitor cells will hereinafter be referred to as the "stem cells." Therefore, all of mammalian hematopoietic cells can, in theory, be derived from a single stem cell. The stem cell is able to self-renew, so as to maintain a continuous source of pluripotent cells. In addition, when subject to particular environments and/or factors, the stem cells may differentiate to yield dedicated progenitor cells, which in turn may serve as the ancestor cells to a limited number of blood cell types. These ancestor cells will go through a number of stages before ultimately yielding a mature cell. Stem cells may be related to the lympho-hematopoietic system. Other stem cells may be unrelated to the lympho-hematopoietic system and may be derived from ectoderm, mesoderm, and endoderm. These stem cells may include germ cells such as, but not limited to, oogonia and spermatogonia, as well as myoblasts, fibroblasts, osteoblasts and neuroblasts.

The benefit of obtaining a pure population of stem cells is most readily recognized in the field of gene therapy. Briefly, gene therapy can be used to treat specific diseases caused by a defect in a particular gene. For example, sickle cell anemia is caused by a defect in a single gene. The cellular precursors of erythrocytes of sickle cell patients contain this defective gene which, in turn, codes for a defective form of the protein hemoglobin. The defective form results in the clinical condition of sickle cell anemia. Sickle cell anemia cannot be "cured" by conventional drug therapies because the underlying defect is in the gene which is included within every cell. Gene therapy seeks to replace or repopulate the cells of the hematopoietic system with cells that do not contain the defective gene but instead contain a "normal" gene. Using conventional recombinant DNA techniques, a "normal" gene is isolated, placed into a viral vector, and the viral vector is transfected into a cell capable of expressing the product coded for by the gene. The cell then must be introduced into the patient. If the "normal" gene product is produced, the patient is "cured" of the condition.

Bone marrow transplantation is an effective therapy for an increasing number of diseases. Graft Versus Host Disease (GVHD), however, limits bone marrow transplantation to recipients with histocompatibility (HLA)-matched sibling donors. Even then, approximately half of the allogenic bone marrow transplantation recipients develop GVHD. Current therapy for GVHD is imperfect and the disease can be disfiguring and/or lethal. Thus, risk of GVHD restricts the use of bone marrow transplantation to patients with otherwise fatal diseases, such as malignancies, severe aplastic anemia, and congenital immunodeficiency states.

Less than 1000 bone marrow transplantations per year are currently performed in the United States. Many other patients have diseases that might be treated by marrow cell transplantation (such as sickle cell anemia) if GVHD were not such a serious risk. The potential benefits from expanded use of bone marrow transplantation have stimulated research on the cause and prevention of GVHD. It has been shown that donor T lymphocytes cause GVHD in animals. Removal of T lymphocytes from donor marrow inocula ("grafts") prevented the subsequent development of GVHD in mice, dogs and monkeys. Similar trials in humans with monoclonal antibodies against human T lymphocytes are now in progress. Preliminary results, however, suggest only attenuation of GVHD, not a cure. Similar results have been achieved with E-rosette and soybean lectin depletion of T lymphocytes.

Another approach under investigation is the use of anti-T lymphocyte monoclonal antibodies conjugated to toxins, such as ricin. As of yet, however, GVHD has not been prevented or cured in bone marrow recipients. A continuing need exists, therefore, for new methods of collecting stem cells. Donors of bone marrow are also faced with undesirable procedures and risks. The current procedures for harvesting bone marrow are expensive and painful. Furthermore, the current donation procedure is accompanied by the risks associated with anesthesia, analgesia, blood transfusion and possible infection. It would be desirable, therefore, to improve the current method of harvesting marrow from donors.

Selection, Growth and Differentiation of Cells

In addition to the needs for harvesting specific cell types and isolating a wide variety of other analytes, there is also a need to provide specific substrates for cell adhesion, growth and differentiation. Current substrates for attachment and growth of cells in vitro include poly-L-lysine, fibronectin and other molecules. These substrates are primarily passive in nature, and cell growth and differentiation depends on other factors added to the culture medium such as growth factors, cytokines and hormones. These substrates are not capable of being engineered to optimize specific cell adhesion, growth and differentiation. These substrates also lack the capability to select specific cells from a heterogeneous population of cells and to promote the growth and differentiation of these specific cells.

In addition to a need for isolation and controlled differentiation and growth of stem cells that are related to the hematopoietic system, as described above, there is also a need for the isolation, controlled differentiation and growth of stem cells which are not associated with the hematopoietic system. Such stem cells may be derived from ectoderm, mesoderm, and endoderm. These stem cells may include germ cells such as oogonia and spermatogonia, myoblasts, fibroblasts, osteoblasts and neuroblasts.

What is needed are polymer membranes that have characteristic and specific properties for cell adhesion, growth and differentiation. What is also needed are polymer membranes that may be specifically designed and controlled to possess characteristic properties for cell selection, adhesion, growth and differentiation.

SUMMARY OF THE INVENTION

In its broadest respects, the present invention is a biologically-active polymer composition and method for detecting, isolating and/or purifying an analyte. The analyte can be found in a liquid in soluble or insoluble form or it can be a particle in a liquid. The analyte may also be in a gas phase. Analytes that can be detected, purified or isolated according to the present invention include, but are not limited to, atoms, ions, molecules, cells, cell organelles, and other particulates. In one preferred embodiment of the present invention, the composition and method are used to isolate stem cells from a suspension of cells collected from blood or bone marrow.

In another aspect, the biologically-active polymer of the present invention is a composition and method for making polymer membranes that have characteristic and specific properties for cell adhesion, growth and differentiation. These polymer membranes may be specifically designed and controlled to possess characteristic properties for cell adhesion, growth and differentiation.

Thus, in one embodiment, the biologically-active polymer of the present invention provides a method of isolating and purifying immature bone marrow cells. The present invention provides a composition and method for preparing a cell population useful for stem cell transplantation that is substantially pure immature marrow cells and substantially free of mature myeloid and lymphoid cells. The present invention also provides a method of collecting donations useful for stem cell transplantation that avoids the disadvantages of conventional marrow harvesting techniques. The present invention provides a therapeutic method of transplanting stem cells that can extend the use of stem cell transplantation to the treatment of non-fatal diseases.

These and other objects of the present invention are achieved by one or more of the following embodiments. One embodiment of the present invention provides a suspension of human cells comprising pluripotent lympho-hematopoietic stem cells substantially free of mature lymphoid and myeloid, cells, as well as therapeutic methods employing such a cell suspension.

In another embodiment, the present invention may be used to isolate stem cells unrelated to the lympho-hematopoietic system. These stem cells may be derived from ectoderm, mesoderm, and endoderm. These stem cells may include germ cells such as, but not limited to, oogonia and spermatogonia, myoblasts, fibroblasts, osteoblasts and neuroblasts.

The biologically-active polymer of the present invention provides a polymer film that is capable of specifically binding an analyte, such as a stem cell. Although not essential in the practice of the present invention, when a voltage is applied to the polymer film binding of the analyte can be increased. The bound stem cell can then be released by reversing the voltage across the film. The present invention also includes an electrolyte that can be used to capture the analyte on the polymer film. The present invention also encompasses a method of making the polymer film that is capable of specifically capturing an analyte.

In one embodiment, the polymer film of the present invention has antibodies incorporated therein so that, when a voltage is applied across the polymer film, the antibodies will bind the analyte to which the antibody is directed. Some antibodies or other analytes require a certain background current to bind antigens or analyte recognition molecules, respectively. Next, the voltage is partially or completely reversed, the antibodies are no longer capable of binding the analyte, and any analyte that was bound to the antibodies bound to the polymer film is partially or completely released depending on the degree of voltage reversal. These analytes may be in a gaseous phase, in a liquid phase, in solution, insoluble, and possibly not bound to another entity. Alternatively, these analytes may be bound to other molecules, organelles and cells in a manner that permits recognition by the antibody bound to the polymer film.

In another embodiment, a polymer film can be prepared that does not have any antibody incorporated therein, but can still specifically bind to an analyte normally recognized by the antibody. In preparing the polymer film, an antibody (or other molecule) that specifically recognizes the desired analyte is used to impart to the polymer film the ability to recognize and bind the analyte. The antibody is then released from the polymer film, but the film itself can still recognize the analyte.

It is to be understood that non-antibody analytes can be used to impart recognition capability to the polymer film for any other analyte that is recognizable by the analyte used to impart recognition capability. Accordingly, in another embodiment of the present invention, an analyte such as a biological molecule is used to impart to the polymer film the ability to recognize and bind any antibody, receptor, organelle or cell surface molecule that is normally recognized by the biological molecule used to impart recognition capability to the polymer film.

It is also understood that the scope of the present invention is not limited to biological molecules or biological analytes. Any molecule may be employed to impart recognition capability to the polymer film. Accordingly the present invention encompasses the ability to use these films to bind all atoms, ions, molecules, inorganic molecules, organic molecules and complexes of inorganic and organic molecules.

In another embodiment of the present invention, several polymer films, each specific for an individual analyte are arranged in series or matrix to provide the ability to perform multiple analyte determinations in a single sample. These polymer films may be located in a patient or employed in vitro. The data from these membranes may be displayed, printed, stored in a data storage means, input into a computer, sent to a remote data storage means or a computer, or input into a trained neural network. This embodiment is also present in the form of an easy to use home test kit which is configured to provide data to or about the patient, and may also be configured to transmit the data to a remote location such as the office of a health care provider, a health maintenance organization, a hospital, a centralized data analysis facility, or elsewhere.

In another embodiment of the invention, the analyte-detection polymer films may be arranged in a configuration so that electrically activated flow gates are located at the outflow side of the sample transmission tube. Since each polymer film can detect the analyte in a very short time and transmit this information to a computer, the computer can be programmed to open or close the flow gate depending on the next analyte that should be measured. For example, in the differential diagnosis of a particular condition involving several variables, detection of analyte A at a certain concentration X might indicate that the measurement of analyte C should be performed and not analyte B. If analyte C were present at a threshold concentration then analyte D should be measured and not analyte E. A computer programmed in this fashion would receive the results from polymer film A as indicating a concentration greater than or equal to X and then open gate A to direct the sample flow to polymer film C. If the measurement at polymer film C were below threshold, then the computer would open gate C to direct sample flow to polymer film E.

It is also within the scope of the present invention to employ trained neural networks housed in a computer to analyze patterns in the data obtained from the detection and measurement of analytes. These trained neural networks assist the health care provider in the analysis of the analyte data output of the analyte detection polymer films.

Still a further embodiment of the present invention involves a polymer film, or series of polymer films to which specific substances are reversibly bound. Such polymer films may be implanted into a patient or used in vitro. These polymer films release substances upon activation through changes in voltage. Furthermore, the amount and duration of substance released may be adjusted by altering the signal to the polymer film.

Yet another embodiment of the present invention is a system for detection and measurement of analytes and subsequent release of substances which may provide a therapeutic or other desired effect.

Accordingly, it is an object of the present invention to provide a polymer film that is capable of binding a specific analyte and, when desired, will release the analyte from the polymer film.

It is a further object of the present invention to provide a polymer film that can quantitatively or qualitatively detect the presence of an analyte.

Another object of the present invention is to provide a device comprising an assembly of several polymer films, each specifically designed to bind an analyte, so that several analytes may be measured in a single sample.

Another object of the present invention is to provide a device comprising an assembly of several polymer films, each specifically designed to bind an analyte, so that several analytes may be measured in a single sample, wherein the degree of binding is measured as a change in voltage which is output to a data storage device which may optionally analyze the data and optionally transmit the results to a nearby or remote data receiving station for inspection by a health care provider.

It is another object of the present invention to provide a plurality of analyte specific polymer films in a sample flow through system equipped with computer activated gates positioned on the outflow side of the polymer film such that a computer may direct the flow of sample to specific polymer films.

Yet another object of the present invention is to provide a device for home use comprising several polymer films, each specifically designed to bind an analyte, so that several analytes may be measured in a single sample.

Still another object of the present invention is to provide for the analysis of data produced from a plurality of analyte specific polymer films.

It is another object of the present invention to provide a polymer film that is capable of binding and collecting analytes, thereby providing a means to isolate and purify analytes.

Another object of the present invention is to provide a polymer film that is capable of releasing substances upon electrical stimulation of the polymer film.

It is another object of the present invention to provide a polymer film that can be implanted within a patient and is capable of releasing substances upon electrical stimulation of the polymer film.

It is another object of the present invention to provide a polymer film that is capable of binding cells and releasing them when the polymer film is activated electrically.

It is another object of the present invention to provide a polymer film that is capable of binding and collecting stem cells.

It is another object of the present invention to provide a polymer film that is capable of binding and collecting lymphohematopoietic stem cells.

It is another object of the present invention to provide a polymer film that is capable of binding and collecting bacteria.

Another object of the present invention is to provide polymer membranes that bind cells and a method for making these polymer membranes.

It is further an object of the present invention to provide polymer membranes that bind cells and promote cell growth and a method for making these polymer membranes.

It is further an object of the present invention to provide polymer membranes that bind cells and promote cell growth and differentiation and a method for making these polymer membranes.

It is an object of the present invention to provide polymer membranes that have characteristic and preselected properties for cell adhesion, growth and differentiation and a method for making these polymer membranes.

It is further an object of the present invention to provide polymer membranes and a method for making polymer membranes that favor the growth and differentiation of a homogeneous population of cells when initially exposed to a stem cell population.

It is another object of the present invention to provide polymer membranes and a method for making polymer membranes that favor the selection of a specific type of cell when initially exposed to a heterogeneous population of cells.

It is another object of the present invention to provide polymer membranes and a method for making polymer membranes that favor the selection and growth of a specific type of cell when initially exposed to a heterogeneous population of cells.

Still another object of the present invention to provide polymer membranes and a method for making polymer membranes that favor the selection, growth and differentiation of a specific type of cell when initially exposed to a heterogeneous population of cells.

It is yet another object of the present invention to provide polymer membranes and a method for making polymer membranes that favor a specific type of growth and differentiation of cells.

It is another object of the present invention to provide a method by which the polymer membranes can be controlled electrically to induce controlled cellular differentiation and modulate the cell growth cycle.

These and other objects, features and advantages of the present invention will become apparent after a review of the following detailed description of the disclosed embodiments.

DETAILED DESCRIPTION

Figure 1:
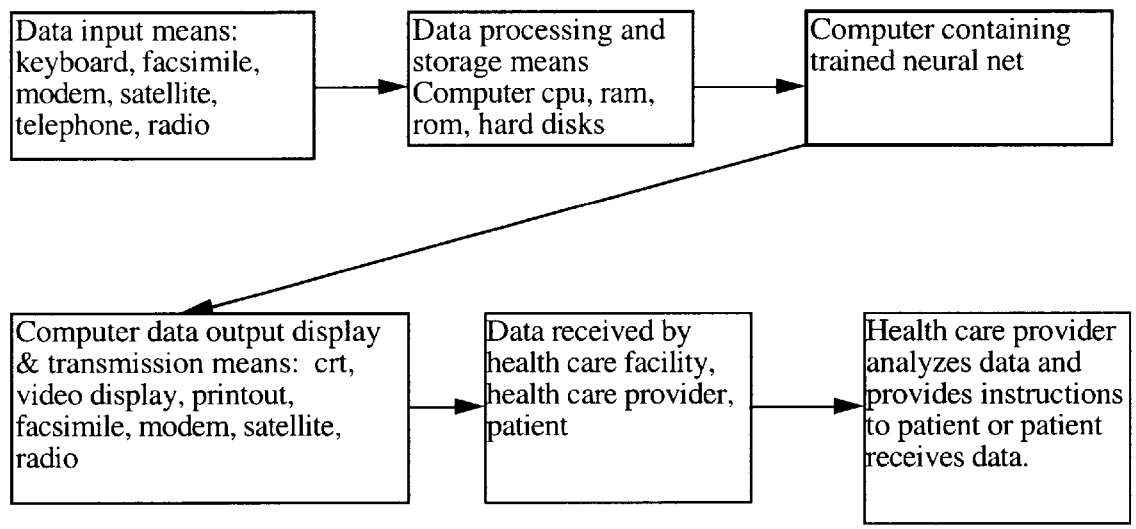
FIG. 1 is a schematic diagram of the means employed to input, process, and analyze data using a computer housing a trained neural network, and to transmit the output to the health care facility.

The following patent applications are incorporated herein in their entirety; U.S. provisional patent application Ser. No. 60/004,757 filed on Oct. 2, 1995, U.S. non-provisional patent application Ser. No. 08/599,888 filed on Feb. 12, 1996, and U.S. provisional patent application Ser. No. 60/022,825 filed on Jul. 26, 1996.

The term "patient" is employed to mean any living organism including, but not limited to, humans and animals including, but not limited to, pets, farm animals, livestock, fish, and birds.

The term "health care provider" means any individual responsible for the health of a patient. Health care providers include but are not limited to physicians, veterinarians, nurses, physician assistants, nursing assistants, chiropractors, psychiatrists, homeopaths and the like.

By the term "health care facility" is meant any facility which evaluates the health status of a patient or administers or recommends a therapy. Examples of health care facilities include hospitals, health maintenance organizations, clinics, and offices of physicians, veterinarians, nurses, chiropractors, psychiatrists, homeopaths and the like.

The term "sample" means any biological, chemical, or environmental fluid, gas, tissue or extract of any fluid, gas, or tissue. Examples of samples which may be obtained from biological samples including fluids such as urine, saliva, sputum, cerebrospinal, gastrointestinal, biliary, pleural, peritoneal, systemic venous, portal venous, arterial, urinary, lymphatic, intracellular, extracellular, and fluids of the male and female reproductive systems, including but not limited to, follicular, menstrual, bulbourethral, amniotic, testicular, seminal, ejaculatory and prostatic fluids. Other biological fluids may consist of extracts of cell, tissues and organs of plants and animals. Environmental samples may be air, water, earth and its fluids and extracts. Chemical samples may include any gas or liquid or extract thereof.

The term "analyte", as used herein, means an atom, ion, molecule, macromolecule, organelle, or cell that is detected and measured by binding of the analyte to the film or to molecules bound to the film. Analytes include molecules, such as proteins, glycoproteins, metal salts, ions, and the like. The term analyte also includes neurotransmitters, hormones, growth factors, cytokines, monokines, lymphokines, nutrients, enzymes, and receptors. The term analyte also means structured elements such as macromolecular structures, organelles and cells, including, but not limited to cells of ectodermal, mesodermal, and endodermal origin such as stem cells, blood cells, neural cells, immune cells, and gastrointestinal cells, and also microorganisms, such as fungi, viruses, bacteria, including but not limited to gram positive and gram negative bacteria, and protozoa. The term analyte also means antimicrobial agents, including but not limited to, rifampin, isoniazid, ethambutol, gentamicin, tetracycline, erythromycin, pyrazinamide, streptomycin, clofazimine, rifabutin, fluoroquinolones such as ofloxacin and sparfloxacin, azithromycin, clarithromycin, dapsone, doxycyline, ciprofloxacin, ampicillin, amphotericin B, fluconazole, ketoconazole, fluconazole, pyrimethamine, sulfadiazine, clindamycin, azithromycin, paromycin, diclazaril, clarithromycin, atovaquone, pentamidine, acyclovir, trifluorouridine, AZT, DDI, DDC, and other antiviral nucleoside analogs, foscornat, ganciclovir, viral protease inhibitors, antisense and other modified oligonucleotides, and ribavirin.

The term "growth", as used herein, means any increase in the number of cells or in the size of the cell or a component of the cell. Accordingly, growth encompasses an increase in cell division through mitosis or meiosis, an acceleration of the cell growth cycle, and an increase in the cell membrane or in any cellular organelle or process. For example, the term growth includes an increase in the number of cells, and an elongation of a cellular process. A cellular process includes, but is not limited to processes such as axons, dendrites, pseudopods, cilia, sensory endings, and flagella.

The term "differentiation", as used herein, means any increase in the degree of commitment of the cell to a specific fate or specialization. For example, differentiation of a bone marrow stem cell would include any further commitment of the cell to a monoblast, myeloblast, megakaryoblast, lymphoblast, plasmoblast or rubriblast. In another example, differentiation of a neural progenitor cell, or neuroblast, would include any further commitment of the cell to develop into a specific type of neuron. Accordingly, the term "differentiation", as used herein, includes the potential of all pluripotent stem or blast cells to produce more specialized cells. Examples of pluripotent stem or blast cells include, but are not limited to, endodermal cells, ectodermal cells, and mesodermal cells. Pluripotent stem or blast cells also include, but are not limited to, bone marrow stem cells, mesenchymal cells, neuroepithelial cells, neuroblasts, glioblasts, osteoblasts, germ cells, myoblasts, and cells obtained from umbilical cord blood.

In its broadest respects, the present invention is a biologically-active polymer film that can specifically bind an analyte, determine the amount of analyte that is bound, and also release the analyte from the polymer film in response to a signal. The desired signal is the change in impedance of an electric current placed across the film when the analyte binds to the film. Other signals may be a change in the ionic strength of the solution surrounding the film or the introduction of a specific molecule into the environment around the film. It is to be understood that the biologically-active polymer films of the present invention may optionally be made from pyrrole, thiophene, or aniline, or from combinations of thiophene, aniline, and/or pyrrole. By the term "thiophene" is meant all substitutions and derivatives of thiophene. By the term "aniline" is meant all substitutions and derivatives of aniline. By the term "pyrrole" is meant all substitutions and derivatives of pyrrole.

The biologically-active polymer of the present invention is also polymer film that can specifically bind a substance and also release the substance upon electrical activation of the polymer film. The term "substance", as used herein, means an atom, ion, molecule, macromolecule, organelle, or cell which is released from the film or from molecules bound to the film. Substances include molecules, such as organic and inorganic molecules, peptides, proteins, glycoproteins, carbohydrates, nucleic acids, lipids, metal salts, ions, and the like. Substances also include but are not limited to neurotransmitters, hormones, growth factors, antineoplastic agents, cytokines, monokines, lymphokines, nutrients, enzymes, receptors, antibacterial agents, antiviral agents, antifungal agents, and antineoplastic agents. Typical antineoplastic agents include, but are not limited to, antimetabolites such as folate antagonist, methotrexate, purine antagonist 6-mercaptopurine, pyrimidine antagonist 5-fluorouracil, cytarabine; alkylating agents such as mechlorethamine, chlorambucil, cyclophosphamide, melphalan, ifosfamide; plant alkaloids such as vincas, vinblastine, vincristine, colchicine, podophyllotoxins etoposide; antibiotics such as doxorubicin, bleomycin, mitomycin; nitrosureas such as carmustine, lomustine; inorganic ions such as cisplatin; substances such as taxol and metalloproteinase inhibitors; protease inhibitors; and hormones such as tamoxifen, and glutamide. The term substance also means structured elements such as cells, including all animal and plant cells, especially stem cells and blood cells, and microorganisms, such as fungi, viruses, bacteria including but not limited to all gram positive and gram negative bacteria, and protozoa. The term substance also means organelles and macromolecular entities such as components of organelles and cells. The terms "substance" and "analyte" may be used interchangeably in this application. An amount of electrical activation effective to release a substance or analyte from the biologically-active polymer is that voltage or voltage change required to release the substance or analyte, about 0.1 to 2.0 V.

The biologically-active polymer of the present invention also encompasses multiple polymer films, each specific for binding an analyte and/or releasing a substance. The selection and arrangement of multiple polymer films permits the detection and measurement of several analytes. Such data might be relevant for the diagnosis of a particular condition or disease state. The use of multiple polymer films also permits the administration of several substances in vivo and in vitro, and also enables the administration of substances at particular times, for specific durations and in defined amounts.

The present invention provides compositions comprising biologically-active polymer membranes and methods for making biologically-active polymer membranes that act as cell growth substrates. These biologically-active polymer membranes may be specifically designed to selectively bind cells and specific cell types, to affect cell growth characteristics, and to modulate cellular differentiation. These biologically-active polymer membranes may be controlled electrically to induce controlled cellular differentiation and modulate the cell growth cycle.

It is to be understood that the practice of the present invention provides the ability to specifically alter the characteristics of the biologically-active polymer membranes. By altering the voltages as described in the examples provided in this application, the characteristics of the biologically-active polymer membrane may be changed. Specifically, starting with a high voltage and reducing it over time in different voltage steps and for different durations will alter the cell binding and growth characteristics of the synthesized biologically-active polymer membrane. Alternatively, starting with a low voltage and increasing it over time in different steps and for different durations will alter the cell binding and growth characteristics of the synthesized polymer membrane. It is contemplated as part of this invention that numerous permutations in the magnitude of the voltage steps, in the duration at each voltage, and in the overall increase or decrease in the voltage may be employed to make selective membranes with characteristic properties for binding cells and affecting their growth and differentiation.

It is also to be understood that the present invention may be used to synthesize biologically-active polymer membranes that are specific for different cell types. Accordingly, biologically-active polymer membranes may be synthesized that will bind any cell type and promote its growth and differentiation, optionally in specific patterns of growth and differentiation.

It is also understood that control of cell growth and differentiation can be achieved with the use of different electric currents and/or in the presence of special reagents.

The biologically-active polymer of the present invention includes optionally a pyrrole polymer film that is formed in the presence of an antibody. By the term "pyrrole" is meant all substitutions and derivatives of pyrrole. The pyrrole polymer is preferably polymerized on a conductive substrate such as indium tin oxide glass. After polymerization, the antibodies in the polymer film are capable of binding to a specific analyte. Unexpectedly, when a current is applied across the polymer, the antibodies have an increased binding capability. When the current across the biologically-active polymer is reversed, the bound analyte is released from the antibody bound to the biologically-active polymer film.

In another embodiment of the present invention, the pyrrole is polymerized in the presence of the antibodies. After the pyrrole is polymerized, an electric current is applied across the polymer film while the polymer is titrated with a solution of sodium chloride. The sodium chloride is added until there is sharp change in impedance. The polymer film is then immersed in a solution containing thiophene (Aldrich) and a current is applied across the polymer. Antibodies are then added to the solution surrounding the indium tin oxide plate.

After approximately 15 minutes, the plate is removed and carefully washed. The current is then reversed and the antibodies are released from the polymer. However, a portion of the polymer film is essentially the three dimensional shape or a model of the antibody and is therefore capable of specifically binding the analyte, in this case an antigen, against which the antibody was specifically generated. While not wanting to be bound by this theory, it is believed that application of current to the film changes the electrostatic field near the model and alters the binding capability of the model. Using this process, polymer film models may be made from any analyte, not just antibodies, and polymer films can be designed with recognition capability for any atom, ion, molecule, macromolecule, organelle, or cell that binds to the analyte used to impart recognition capability to the polymer film.

In another method of making a biologically-active polymer film that recognizes analytes, enzymes are employed to catalyze the interaction between the polymer film and analyte.

It is to be understood that the present invention can be used to detect or isolate a wide variety of analytes. In addition, when the analyte binds to the antibody that is immobilized in the polymer, or to the three dimensional polymer film model of the antibody or other analyte that imparts recognition capability to the film, the binding can be detected electrically. The voltages (conductivities) of the film are measured before (initial voltage) and after binding (final voltage) of the analyte and compared to each other to produce a voltage differential. Following electrical detection of the bound analyte, the amount of binding can be analyzed in different ways including computer analysis of the binding (voltage differential) relative to known amounts of binding using standard concentrations of the analyte and the resultant conductivity changes. This information is stored, displayed or transmitted via different means to other data storage devices and computers. The information may be analyzed using a trained neural network contained within a computer in order to facilitate recognition of patterns in the data. This analysis facilitates the interpretation of data and would assist the users of the data. For example, the analysis aids health care providers in evaluating data obtained from patient samples and forming diagnoses, prognoses, and in developing a therapeutic strategy.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE I
Preparation of Polymer With Antibodies

To 20 mls of pure acetonitrile add 1 ml of $H_2O$ until a saturated solution is obtained. Add 5 mls of naphthalene-2-sulfonic acid sodium salt. A solution of 1 M KOH is added until a pH of 5.5 is obtained An indium tin oxide glass (Meadowlark Optics, Longmet Colo.) is attached to a constant voltage battery. 2 ml of double distilled pyrrole (Aldrich) is then added. Antibody is then added to the solution at a concentration of 0.25 to 1 $\mu$g/ml. For a polymer film that captures stem cells, the antibody is CD-34 (Johns Hopkins University, Baltimore, Md.). 1.5 volts is applied to the indium tin oxide glass electrode for 30 seconds and then lowered to 0.9 to 1 volts for 15 to 20 minutes. The plate is then removed from the polymer solution and rinsed with distilled water.

EXAMPLE II
Preparation of the Electrolyte

To 30 mns of an 0.1 M acetonitrile solution, add 2 mls of 0.1 M tetraacetyl ammonium-4-toluene sulfonate. This solution is added to 30 mls of minimum essential medium (MEM) tissue culture medium. The final pH of the electrolyte solution is 6.0.

EXAMPLE III
Method of Capturing Stem Cells

Blood was collected from a human volunteer. The blood was suspended in MEM tissue culture medium from Example II at a concentration of 100 mls of blood per liter of tissue culture medium. The polymer coated indium tin oxide electrode with the CD-34 antibodies (U.S. Pat. No. 5,035,994 which is incorporated herein in its entirety by reference) attached thereto from Example I was placed in the electrolyte tissue culture medium containing the blood. A voltage of 1 volt was applied to the electrode for 30 seconds. The electrode was then removed from the MEM tissue culture medium and gently washed in fresh tissue culture medium at a temperature of 37° C. Microscopic examination of the polymer coated electrode showed that only stem cells were attached to the polymer. After washing, the electrode was then placed in fresh medium and the voltage across the electrode was reversed. The stem cells that were attached to the polymer were released and collected in the tissue culture medium.

EXAMPLE IV
Preparation of Antigen-specific Polymer

To 20 mls of pure acetonitrile add 1 ml of $H_2O$ until a saturated solution is obtained. Add 5 mls of naphthalene-2-sulfonic acid sodium salt. A solution of 1 M KOH is added until a pH of 5.5 is obtained An indium tin oxide glass (Meadowlark Optics, Longmet Colo.) is attached to a constant voltage battery. 2 ml of double distilled pyrrole (Aldrich) is then added. 1.5 volts is applied to the indium tin oxide glass electrode for 30 seconds and this is lowered to 0.9 to 1 volts for 15 to 20 minutes. At this point, the polymer solution is titrated with 0.1 M NaCl until there is a sharp impedance change. This impedance change will typically occur between the addition of approximately 1 $\mu L$ and 10 $\mu L$ of the NaCl solution. The plate is then immersed in a solution containing 2 mls thiophene with 20 mls of 5% aqueous acetonitrile solution and 5 mls of electrolyte solution of Example II and a voltage of 1 is applied to the plate. Antibodies are then added to the solution at a concentration of 0.25 to 1 $\mu g/ml$ and 0.8 to 0.9 volts is applied to the plate for 15 minutes. The voltage across the plate is then reversed and the antibodies are released. The plate is then removed from the polymer solution and rinsed with distilled water.

EXAMPLE V
Binding of Stem Cells to the Thiophene Plate and Their Subsequent Release Blood was collected from a human volunteer. The blood was suspended in MEM tissue culture medium from Example II at a concentration of 100 mls of blood per liter of tissue culture medium. The indium tin oxide electrode coated with polymer bound to the CD-34 antibodies (U.S. Pat. No. 5,035,994 which is incorporated herein in its entirety by reference) attached thereto from Example I was placed in the electrolyte tissue culture medium containing the blood. A voltage of 1 volt was applied to the electrode for 30 seconds. The electrode was then removed from the MEM tissue culture medium and gently washed in fresh tissue culture medium at a temperature of 37° C. Microscopic examination of the electrode showed that only stem cells were attached to the polymer film. After washing, the electrode was then placed in fresh tissue culture medium and the voltage across the electrode was reversed. The stem cells that were attached to the polymer coated electrode were released from the polymer and collected in the tissue culture medium.

EXAMPLE VI
Analyte Assay System

In one embodiment of the invention, Fc fragments of antibodies are linked to the polymer film such that the Fab fragments, specific for a particular antigens, are available for binding to the antigen. The size of the film and the density of Fc fragments bound per unit area are adjusted according to the desired application. The film is coupled to a power transmitting means and also to a recording means. In this fashion, the resistance or conductivity of the film may be measured and monitored continuously. The monitoring means consists of any electrically coupled means which receives an signal from the film concerning the conductivity or resistance of the film and displays, records and/or transmits this information to a receiving means.

In a preferred embodiment of the invention, the film is contacted by the sample containing the analyte of interest, the analyte is bound to the Fab fragments of the antibodies, thereby causing an alteration in the conductivity of the film. This change in conductivity of the film is proportional to the degree of binding of the analyte to the available analyte-binding sites on the antibodies that are bound to the film at their Fc fragments. The proportionality of the binding may be linear, non-linear, sigmoidal or display some other relationship. The binding of analyte contained within samples is quantitated by measuring the change in conductivity of the film. The binding of any particular analyte to specific antisera is characterized by analyzing the binding of various concentrations of known amounts of analytes called standards. The sensitivity and binding capacity of the film is varied by changing the density of antibodies per unit area and by changing the total film area.

The binding of the analytes to the Fab fragments on the film is changed by partially or completely reversing the polarity on the film, or by applying current to the film, or by changing the voltage across the film. Using these methods, the analyte is removed from the film very rapidly using electrical stimulation, thereby providing an analyte-free film surface for the measurement of the next sample.

This embodiment of the present invention permits the capability to measure the amount of analyte in a sample. Samples may be in liquid or gaseous phases. Analytes that can be recognized by antisera can be measured with this invention. This invention also permits the purification of an analyte from a sample. After the analyte is bound to the Fab fragments of the antibody that is linked to the film as described above and then released by changing the voltage, the elution of the analyte provides a preparation of highly enriched and purified analyte. The degree of purification is related to the amount of binding capacity of the membrane and the binding affinity and specificity of the antibodies.

EXAMPLE VII
Multiple Analyte Assay System

In another embodiment of the present invention, the films coated with antibodies as described in Example VI are used in combination to perform multiple analyte determinations on a single sample. In this embodiment, several films, each coated with a different antibody and each linked to conductivity measuring and recording means are placed in series. For example, films are coated individually with antibodies to the following molecules; estrogen and related sex steroids, progesterone, testosterone, follicle stimulating hormone, inhibin, luteinizing hormone releasing hormone and chorionic gonadotropin. A biological sample consisting of plasma isolated from the blood of a patient is passed through a tube or other transmitting means past each of these films. During contact with each polymer film, the analyte recognized by that particular antibody, for example, luteinizing hormone, is bound, resulting in a change in conductivity of the film. The next film might bind estradiol, the next progesterone, and so on until each polymer film is exposed to the plasma sample. Each film displays a conductivity level or value indicating a particular amount of hormone. These values are stored in a computer or other data storage means, sent to another computer or other data storage means, displayed on a screen or printed for evaluation by a person trained to analyze patterns of these specific hormones. Such information is valuable in the assessment of reproductive capability and fertility in order to more accurately predict pregnancy, ovulation and the optimal time for fertilization or avoidance of fertilization, the onset of puberty, the onset of menopause and endocrinopathies associated with the hypothalamus, pituitary gland, ovaries, testes and adrenal gland.

In another embodiment of this example of measurement of reproductive hormones, several antibody-coated films are placed in a test chamber designed to receive small volumes of plasma to facilitate multiple hormone determinations in a single chamber. This embodiment of the present invention avoids the need for sample flow through tubing to transmit plasma from one film to the next. This embodiment may occur in the form of multi-well plates, each containing several films either arranged as individual films or as multiple films inserted in a film receiving device, each film connected electrically to the conductivity measuring means and data storage and analytical means as described above. For example, a multi-well plate containing 72 wells has the capability to perform 72 different hormone measurements simultaneously in singlicate or 36 different hormone measurements simultaneously in duplicate and so on, depending on the choice and arrangement of polymer films. This approach obviates the need for individual assays such as enzyme linked immunosorbant assays (ELISAs) or radioimmunoassays (RIAs) for each hormone in a plasma sample from each patient.

Another embodiment of the multiple analyte detection system is a device or assembly composed of films derived from several different polymer films, each with the capability to detect and measure a different analyte. Such a composite contains individual films in various forms which may be selected based on the application. For example, a disk may be fashioned out of several films, each insulated from each other and connected electrically to transmission means and data processing and storage means. In this manner, a single multiple analyte device detects as many substances as desired. Such composite multiple analyte devices may be placed in multi-well culture plates to detect numerous substances secreted by cells or tissue fragments simultaneously, or placed in vivo to monitor levels of several selected analytes.

Other applications of this multiple analyte determination invention using the films of the present invention include, but are not limited to the following:

evaluation of patients with delayed or precocious puberty (luteinizing hormone releasing hormone, follicle stimulating hormone, luteinizing hormone, inhibin, estrogen and related sex steroids, testosterone and related sex steroids, progesterone, and other molecules);

evaluation of growth in patients of short stature (analysis of growth hormone, somatomedins, growth factors, growth hormone releasing hormone, thyroid hormones, adrenal steroids, somatostatin, anabolic steroids and other molecules);

evaluation of suspected diabetic patients (glucose, insulin, somatostatin, glucagon, growth hormone, and other molecules);

adrenal gland dysfunction (glucocorticoids, dehydroepiandrosterone, aldosterone, deoxycortisol, corticosteroid, hydroxyprogesterone and other sex steroids, adrenocorticotropin, corticotropin releasing hormone and other peptides, catecholamines (norepinephrine and epinephrine), renin, opioids, and other molecules);

thyroid gland function (thyroxine, triiodothyronines, thyroid stimulating hormone, thyrotropin releasing hormone, and other molecules);

parathyroid gland function (parathyroid hormone, calcitonin, phosphorus, calcium and other molecules);

cardiovascular function (triglycerides, cholesterol, high density lipoprotein, low density lipoprotein, lipids, and other molecules);

kidney function and water balance (vasopressin (antidiuretic hormone), renin, aldosterone, atrial natriuretic hormone, sodium, potassium, creatinine, ammonia, calcium, and other molecules);

evaluation of pancreatic endocrine function (somatostatin, glucagon, insulin, pancreatic polypeptide, amyloid and other molecules);

evaluation of hypothalamic function (luteinizing hormone releasing hormone, vasopressin, oxytocin, somatostatin, thyroid hormone releasing hormone, growth hormone releasing hormone, opioids, neuropeptide Y, cholecystokinin, corticotropin releasing hormone, neurotensin, vasoactive intestinal peptide, peptide histidine isoleucine, gastrin, substance P, dopamine, norepinephrine, serotonin and other molecules);

evaluation of pituitary function (growth hormone, luteinizing hormone, follicle stimulating hormone, thyroid stimulating hormone, adrenocorticotrophic hormone, prolactin, vasopressin, proopiomelanocortin and fragments thereof, oxytocin, and other molecules);

evaluation of immune function (cytokines, lymphokines, monokines, thymosins, adrenocorticotrophic hormone, glucocorticoids, prolactin, growth factors, tumor necrosis factor, and other molecules);

evaluation of rejection following transplantation of biological or synthetic material into a patient (cytokines, lymphokines, monokines, and other factors of the immune system indicative of the occurrence of rejection);

evaluation of circulating forms of cardiac muscle proteins and other molecules that are associated with a heart attack;

evaluation of the types and amount of bacteria, including but not limited to all gram positive and gram negative bacteria, viruses, parasites and fungi present in a sample (films coated with antibodies specific for unique epitopes on specific bacteria, viruses, parasites and fungi);

evaluation of the presence and amount of molecules associated with specific cancers;

evaluation of the presence and amount of variants of molecules such as apolipoprotein E that might be associated with the onset of neurological diseases such as Alzheimer's disease; and evaluation of environmental samples of water, air, plants and earth for the presence of analytes, including, but not limited to bacteria, fungi, parasites, viruses, pollutants, toxins, heavy metals, organic and inorganic molecules.

EXAMPLE VIII

Analyte Assay Kits

It is also within the scope of this invention to provide specific kits for use in the health care facility and in the home. Home test kits include a device for pricking the skin, preferably the skin of the finger in order to obtain a blood sample for analysis in the test kit, a means for delivering the blood sample to the input port of the test kit comprising a single polymer film or multiple polymer films as described above with the capability of measuring one or several analytes, for example, a kit to predict the occurrence of ovulation or to determine if serum levels of molecules associated with heart attack are elevated, a data storage means, optionally a data analysis means, and a data output transmission means. Alternatively, samples are obtained from other biological samples including urine, saliva, sputum, menstrual fluid, fluids of the reproductive system, cerebrospinal fluid, gastrointestinal fluids, pleural fluid, peritoneal fluid, amniotic fluid and also various biological tissues, cells, and extracts thereof. The data resulting from the use of such home test kits can be sent electronically to a health care provider's office so that the health care provider may evaluate the data. Alternatively, an initial processing of the data may be performed by the data storage means such that the output may include a preliminary diagnosis and other forms of data output that might indicate various statistical parameters associated with the diagnosis such as the standard error, power of prediction, variance and other parameters for that particular age group. Various means are used to transmit the data output from the kit including transmission of raw or reduced and analyzed data from the data storage means to the data receiving means (FIG. 1). Such means include a port for linkage to transmitting means, including, but not limited to, facsimile transmission, telephone, cable, modem, satellite links, or other means of communication. For example, the health care provider can evaluate the transmitted data to determine if the patient had a heart attack. Subsequent measures might include instruction to the patient to proceed to a health care facility, to self administer a clot dissolving drug such as streptokinase or tissue plasminogen activator or to take other measures.

In a related embodiment, the home test kit provides immediate data feedback to the patient or recommend a therapeutic course to the patient. For example, the results from the analysis of plasma glucose levels might suggest immediate administration of a certain amount of insulin. In another example, the results from the analysis of a sputum sample might result in a diagnosis of a bacterial infection of the upper respiratory system and suggest that the patient consult a physician to initiate an antibiotic course of treatment.

This system as disclosed in the present invention provides a rapid means to perform multiple determinations of analytes that are associated with different disease states or other medical problems, and to transmit this information to the health care provider for analysis. The net amount of time to obtain a diagnosis and to recommend a therapeutic treatment is greatly reduced thereby providing faster preliminary screening of patients and diagnosis of medical problems. Such improvements may result in vast savings of time, expense and in improved health and longevity.

EXAMPLE IX
Hierarchical Multiple Analyte Detection System

Figure 2:
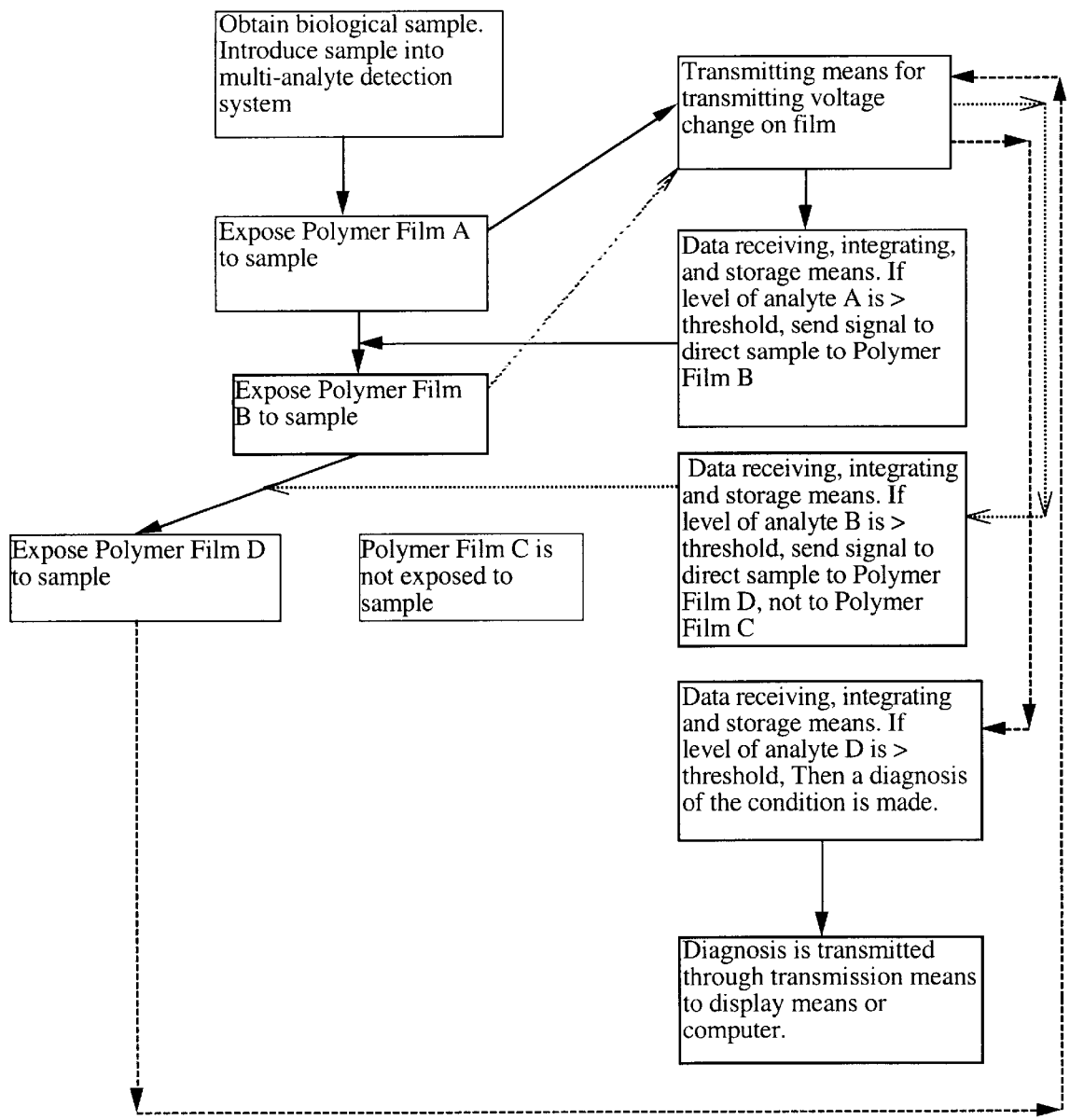
FIG. 2 is a schematic representation of a hierarchical system of analyte specific detection polymer films, the means for transmitting and analyzing the data, the means for directing sample flow to selected polymer films and formulating a diagnostic output.

In a related embodiment of this invention, a biological sample, such as a plasma sample is introduced into a matrix comprising a system of channels that transmit the sample to various polymer films (FIG. 2). Each polymer film is specific for a particular analyte, and access is provided to each film, optionally through membranes that are freely permeable for the analytes measured by the films in the matrix. In this embodiment, branch points or gates are located at the output side of the channel after exposure of the sample to the film. If the result from a particular film is above a certain threshold, indicating the presence of a certain amount of an analyte, then the remaining biological sample could be routed toward a certain film and away from other films that would not provide relevant information. Such a hierarchical branching system provides a series of decision trees, each branch point being activated by an output signal originating from a computer linked to the film recently exposed to the biological sample. For example, in the differential diagnosis of a particular condition, the generic substances A, B, C, and D, are relevant in the formation of an accurate diagnosis. The disease is diagnosed as positive when A, B, and D are present at a particular threshold level. Since the presence of A at a specific threshold concentration is an absolute requirement for the disease, a negative result after the sample is exposed to the A detection film is transmitted as a signal to terminate the subsequent analysis. The output channel after the A film is then routed such that the films dedicated for the measurement of B, C, and D are bypassed. In other words, when A is not present at a certain level there is no point in performing the other determinations.

In another biological sample, A is present above the preset threshold and a signal is sent to the gate at the outflow of film A directing the sample to the B polymer film. However, whenever B is present at a certain level the measurement of C does not provide useful information. Therefore, after the result from the B film indicates the presence of B above the threshold level, the output signal from the B film maintains the closed status of the gate to the C detection film and opens the gate to direct the sample to the D detection film. If the readout from the B film is below threshold, then the gate to the C film opens for exposure of the sample to the C film. If the readout from the D film is above threshold, then a diagnosis of the presence of the condition is made.

This hierarchical multiple analyte detection system provides tremendous savings in the time and expense to perform unnecessary multiple analyte determinations, decreases the amount of biological sample required for a diagnosis by decreasing the amount of sample wasted in the performance of unnecessary tests, and provides a means to accelerate the diagnosis of specific conditions. In addition, after a diagnosis from a given series of films is obtained, the sample may be routed to another series of films designed to diagnose a related condition. For example, after the determination of the presence of an HIV infection through the measurement and analysis of 3 analytes, remaining biological sample may be sent to other film detection systems to determine if specific opportunistic bacterial infections may be present or to determine if specific subsets of cells such as t-lymphocytes may contain certain biological markers.

EXAMPLE X
Neural Network Analysis of Data from Analyte Assay Systems

The data produced from multiple hormone measurements from a sample may be stored in a computer and possibly input into a computer containing a trained neural network. Such a neural network is trained to recognize patterns in the data associated with the specific analytes measured in the system as disclosed. Various commercially available neural network software products such as BRAINMAKER may be utilized recognize patterns within data sets and to facilitate recognition of patterns in the data produced by the multiple analyte measuring system.

As described above, the multiple analyte measuring system produces data in the form of electrical signals that represent the degree of analyte binding. These signals are transmitted to a local or distant data receiving means which in a preferred embodiment is a computer. This computer may contain the trained neural network and the neural network software needed to run the network. The neural network in the computer is trained with a data set derived from patient data in which the variables represented as analytes in the network are weighted according to their contribution to a diagnosis of a particular condition. The data set used to train the neural network contains data from patients with a definitive diagnosis of the disease, such diagnosis being validated by other means including, but not limited to physical examination, cell culture, hematology, virology, microbiology, molecular biology, genetics, radiology, surgery, histology, pathology, and autopsy.

Each variable to be input to the network is represented as an input neuron in the input layer of the neural network. The neural network may contain one or more hidden layers which feed forward and converge to output neurons that provide a value indicative of the presence of a particular medical condition. The output value may be displayed on a computer screen, printed out, or sent to another computer via transmission means. This output value may be evaluated by a health care provider who then decides on a course of treatment.

The neural network is housed in any computer with input means, including but not limited to, keyboard, modem, cable, or tape reader, sufficient memory and operating characteristics to run the neural network software, store the trained neural network, and process the input variables through the trained neural network. Computers which may be used include models such as, but not limited to, IBM, Apple, Dell, Hewlett-Packard, UNIX, and Compaq. These computers are equipped with output transmission means optionally connected to display means including monitors, cathode ray tubes (CRTs) and printers, or to other computers. Such output transmission means include cables, modems, facsimile modems, and internet transmission.

EXAMPLE XI
Films With the Impression of the Fab Fragment of Antibodies

In another embodiment of the present invention, films are produced according to the method of Example IV. Although not wanting to be bound by this statement, it is believed that the antigen binding region of the Fab fragment is modeled in the film in the form of a three dimensional representation of the Fab fragment or of the antigen binding region of the Fab fragment, and that changes in the electrostatic charge of the model affects binding capability. This impression imparts to the film the capability to recognize and bind analytes recognized by the Fab fragment, such as the antigen that the antibody was raised against. This embodiment may be used to isolate analytes such as antigens with a high degree of specificity.

EXAMPLE XII
Films With Analyte Impression

In another embodiment of the present invention, films are produced according to the method of Example IV. Although not wanting to be bound by this statement, it is believed that the a three dimensional representation, or model, of the analyte is made from the polymer film and that changes in the electrostatic charge of the model affects binding capability. This model of the analyte imparts to the film the capability to recognize and bind any molecule that is recognizable by the analyte. This embodiment of the invention is used to isolate antibodies, receptors, binding proteins in solution, or molecules bound to organelles or cells with a high degree of specificity and efficiency. This film may be used in several applications including, but not limited to, affinity chromatography, antibody isolation and purification, receptor isolation, isolation of cells or organelles bearing receptors or other surface molecules, and analyte purification.

EXAMPLE XIII
Plasmapharesis and Other Separations in Biological Fluids

In another embodiment of this invention, film sheets are designed to bind analytes in the blood that are deleterious to the health of a patient. The presence of certain molecules in the blood, including, but not limited to the following; ammonia, potassium, sodium, drugs, alcohol, various bacterial products, metabolites, hormones, cholesterol and related molecules, as well as other molecules, can cause serious health problems under certain circumstances. For example, patients with kidney problems require dialysis of their blood to remove waste products and electrolytes that are injurious to health. Films of the present invention are designed to bind these waste products and electrolytes while permitting erythrocytes and other desirable cells and molecules to remain in the blood for return to the patient.

The films of the present invention may be used not only in cases of kidney dysfunction but also in removing molecules from other fluids, including, but not limited to, peritoneal, pleural, cerebrospinal, synovial, systemic venous, portal venous, arterial, biliary, urinary, lymphatic, gastrointestinal, intracellular, extracellular, and fluids of the male and female reproductive systems, including but not limited to, follicular, menstrual, bulbourethral, amniotic, testicular, seminal, ejaculatory and prostatic fluids.

These films may be utilized ex viva, for example with a venous blood sample removed from a patient with kidney dysfunction in order to remove waste products. The films may also be used within a patient to remove substances. For example, a film may be inserted into the peritoneal cavity to remove cells such as bacteria, viruses, or undesirable bacterial molecules such as endotoxins. Other films can be designed for insertion into the cerebrospinal fluid, for example within the lateral cerebral ventricles, or in the region of the cauda equina. Such a film might be designed to remove contrast agents following a radiographic procedure, to bind bacteria or viruses in cases of meningitis, to bind neurotransmitters, to bind blood components following subarachnoid, subdural or epidural hemorrhage, or to decrease levels of excitatory amino acids following stroke or seizure.

It is to be understood that polymer films are also capable of measuring the analytes bound to them. This capability is useful in assessing the efficiency of analyte binding and removal. This assessment provides a means to monitor levels of analytes to determine if separation and removal of the analyte from the fluid is proceeding in a desirable manner. For example, following head trauma, a polymer film placed in the cerebrospinal fluid provides the ability to detect excitatory amino acids and blood components associated with vasospasm.

Another embodiment of the present invention includes a polymer film coated with analyte binding capability for molecules associated with various tumors such as glioblastomas and astrocytomas or with demyelinating diseases such as multiple sclerosis or Alzheimer's disease. This embodiment may assist in diagnosing these diseases before the clinical manifestations are apparent.

EXAMPLE XIV
Polymer Films as Substance Release Devices

The films of this invention may also be coated with a specific substance for controlled release of the substance. The polymer film may be designed to permit the controlled release of the substance at a chosen rate and for a selected duration. Films may be synthesized so that the substance may be bound to the surface or within a pore in the film so that the substance is relatively protected from enzymatic attack. Substance delivery may be episodic or periodic to mimic, for example, the endogenous growth hormone secretion profiles. In one embodiment, antibodies bound to films at their Fc fragments may bind antigens as described in a preceding Example. This film may be used to deliver the antigen bound to antibody by applying a current to the film surface thereby causing release of the antigen.

Targeted drug delivery is achieved using substance-delivery polymer films by inserting them at or near the desired delivery site. Films are modified to alter their hydrophilicity, hydrophobicity and vulnerability to platelet adhesion and enzymatic attack. Films are arranged in several configurations or assemblies, such as those provided in the following non-limiting examples: as sheets for cutaneous application, subcutaneous or intraperitoneal insertion; as sheets to be wrapped around structures including organs, bones, implants and other prosthetic devices; or as a coating on a cannula, stent or catheter. These films may be connected to a local power source, such as a battery near the film or somewhere else within the body, or a remote power source, such as a battery located outside the body. When substance delivery is desired, a brief pulse of current is provided to alter the potential on the film to cause the release of a particular amount of the substance for a chosen duration. Application of current causes release of a substance from the surface of the film or from an interior location in the film such as within a pore. The rate of substance delivery is altered depending on the degree of substance loading on the film, the voltage applied to the film, and by modifying the chemical synthesis of the substance delivery polymer film.

For example, a film coated with a mitotic inhibitor could be inserted directly into a tumor and the voltage applied to release the mitotic inhibitor directly into the tumor.

In another embodiment, a balloon catheter used in an angioplasty procedure is coated with a polymer film containing molecules that stimulate the healing of endothelial cells. These molecules are released by changing the voltage after the balloon is inflated and before the catheter is withdrawn.

Another embodiment of the present invention includes coating the end of a catheter used in a transurethral prostatic resection procedure with substances that promote the healing of urethral endothelial cells and inhibit the regrowth of prostatic cells. After completion of the resection procedure, a pulse of current deposits the appropriate substances around the catheter within the prostate.

The present invention is also used to release substances in vitro. For example, the polymer films may be designed to bind various growth factors, nutrients, vitamins, antibiotics, amino acids and serum components often used in the culture of cells and tissue fragments. These polymer films may be manufactured in a shape to accommodate the bottom of culture devices such as 72 and 96 well plastic culture plates, or cell culture flasks. These flasks and plates are designed to include connections for the bottom of each well such that an electrical impulse is delivered to the substance laden polymer film at bottom of each well. In this manner, pulses of current delivered to the polymer films cause the release of the vitamins, nutrients or other growth factors from the membrane into the culture medium. These impulses may be delivered in any strength, duration, pattern or at any chosen time interval to maximize cell growth.

Disks are also made from substance containing polymer films which are comprised of sections from several other polymer films, each containing a different substance. These multisubstance disks are inserted into the bottom of a culture plate with conductive properties so that a stimulatory electrical signal causes the release of several substances such as cell growth factors, antibiotics such as penicillin or streptomycin, vitamins, and essential amino acids.

The capability to release substances into culture systems provides significant benefits due to reduced labor and time involved in the manual addition of these substances using pipetting devices. Using this system, culture plates are maintained for longer periods and the addition of required substances may occur automatically from the substance containing polymer films, perhaps through a computer programmed with a dosing schedule. Such substance containing polymer films could also be employed in flow through culture systems to provide required substances.

In another embodiment, substance containing polymer films that bind various drugs, hormones, transmitters or other agents may be used as drug delivery devices in flow-through perfusion systems wherein tissue fragments or cells are maintained in chambers, syringes or on other membranes. Brief electrical stimulation of these substance-containing polymer films facilitate discrete and controlled substance delivery without the need to employ automated or manual culture medium switching devices which can cause problems with pressure differentials, pressure pulsations, and foaming of protein-containing media. This system also eliminates the need for manual addition of the test substance with associated problems such as interrupting flow and imprecise pipetting.

EXAMPLE XV

Combination Analyte Capture and Substance Release System

Figure 3:
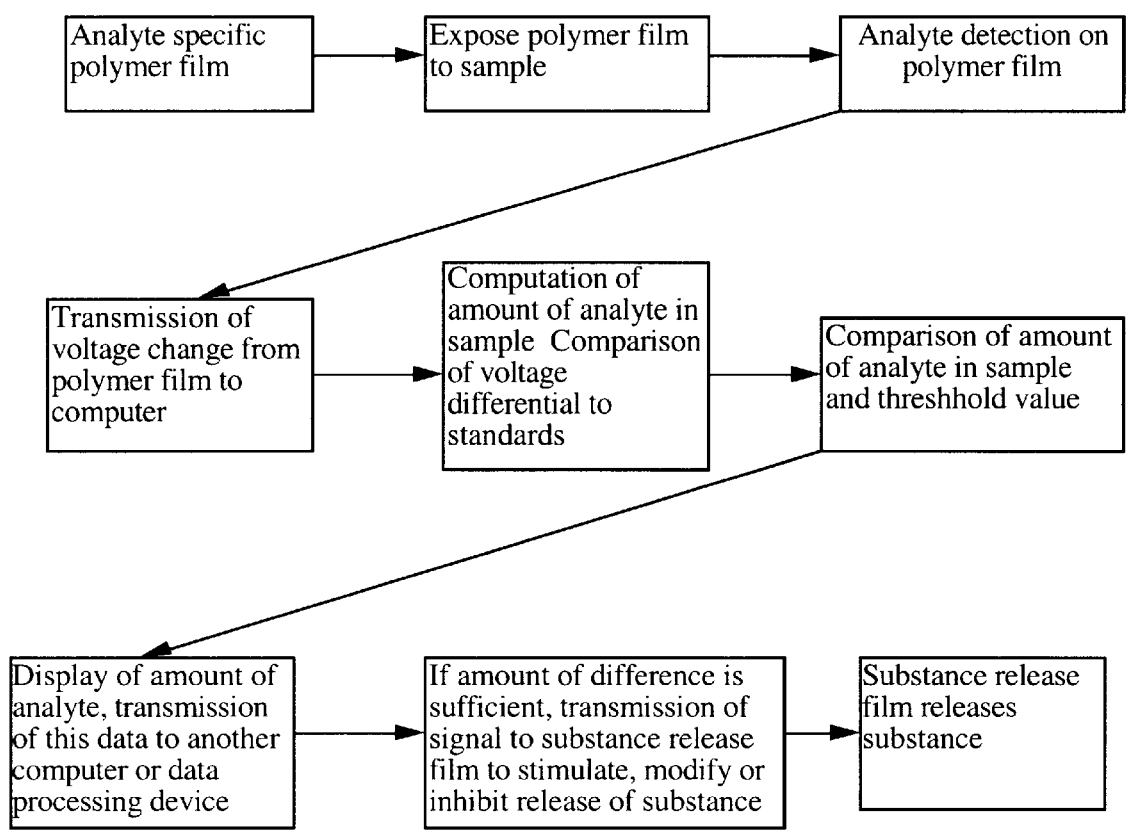
FIG. 3 is a schematic of a system for combined analyte detection and substance release.

In another embodiment of this invention, the embodiments in several of the Examples described above are combined to provide a system for the monitoring and measurement of certain analytes and for the release of certain substances (FIG. 3).

A polymer film coated with antibodies specific for a substance, for example glucose, may be implanted in the bloodstream of a diabetic patient. This analyte detection polymer film binds glucose and the amount of glucose bound is converted into an electrical signal which is interpreted relative to a set of standards to indicate a specific concentration of glucose. If the concentration of glucose exceeds a predetermined threshold, a signal is sent from a computer through transmission means to a substance release polymer film with insulin bound to the polymer film itself or to insulin antibodies bound to the polymer film or to the polymer film model of insulin antibodies. The duration and amplitude of the electrical signal sent to the insulin-coated polymer film are designed to effectuate the release of a specific amount of insulin. As the released insulin stimulates glucose uptake, plasma glucose concentrations decline due to cellular glucose uptake, thereby altering the signal from the glucose-detecting polymer film to the computer.

This system is a promoter of physiologic homeostasis. Similar applications to any physiologic or pathophysiologic system may be used. The system may be configured in different ways depending on the analytes being monitored and the stability, hydophilicity, hydrophobicity, and molecular size of the substance being delivered. Some analytes may be measured transdermally, intradermally, subcutaneously, intravenously, intraperitoneally, intrathecally, intracerebroventricularly and in other anatomical and physiological compartments. Accordingly, this will determine whether the analyte detecting polymer film will be found in a cutaneous patch, in an implant into or below the skin, in an implant within an organ or elsewhere. The biochemical, toxicological, physiological and physical characteristics of the substance being delivered will affect the location of the substance delivery polymer film as well the desire to target substance delivery to a specific region. Lipophilic molecules such as steroids may be delivered through a cutaneous patch containing a steroid delivery polymer film whereas water soluble therapeutic but toxic anti-cancer substances may preferably be delivered through an intravenous line directed to the vascular bed of a tumor or through a catheter directly into the tumor.

Such a system capable of sensing and measuring analytes and then delivering substances provides many advantages. Analytes are measured on-line and a therapeutic is delivered when and where it is optimally utilized. This system saves time and money and promotes rapid and timely therapy. The time lost in making an appointment with the health care provider, traveling to the location of the health care facility, removing a sample, analyzing the sample usually over a period of days and sometimes weeks, waiting for the health care provider to consider the data and recommend a course of therapy, and actually beginning the therapeutic regimen is obviated through the use of the present invention.

This technology may also be used to detect the endogenous hormone rhythms in a patient and to provide supplemental, timed and intermittent hormone or drug replacement therapy. For example, growth hormone is secreted in a specific pattern throughout a 24 hour day. If the peak amplitudes of growth hormone were reduced in a patient, supplementation with synthetic or recombinant growth hormone at these times of peak albeit reduced growth hormone secretion might produce optimal growth stimulating results.

Another example of an application of this invention includes monitoring analytes indicative of a transplant rejection by the immune system. When levels of certain rejection-related immunological molecules reach a threshold level, a signal is sent to another membrane to release immunosuppressants to counteract the rise in the rejection-related immunological molecules. Immunosuppressants are molecules including but not limited to, glucocorticoids and related molecules, cyclosporine, cyclophosphamide, methotrexate, azathioprine, chlorambucil, aspirin, indomethacin, acetaminophen and inhibitors of cyclooxygenase, thromboxane synthase and phospholipase A2 enzymes. Such a system provides a rapid response to immunologic rejection reactions, would prolong the functional life of the implant and decrease the complications resulting from an immunological rejection.

Another embodiment of this invention is a system wherein the membranes are designed to bind to epitopes on bacteria in order to identify the bacterium or bacteria that are present in a sample. The output from such a system of multiple bacterial determinations might be processed to cause a signal to activate a substance release polymer film or several substance release polymer films containing specific antibiotics to release these antibiotics into the bloodstream. This rapid therapeutic response prevents the complications resulting from generalized bacterial infections.

EXAMPLE XVI
Multiple Substance Release System

In another embodiment of the present invention, individual polymer films are loaded with substances chosen for a specific application. Next, the size and shape of a multi-substance delivery vehicle are determined. The dosages of substances to be administered are calculated and the density of substance per film area is measured. The rate of substance delivery may be altered depending on the degree of substance loading on the film, the voltage applied to the film, and by altering the chemical synthesis of the substance delivery polymer film. In view of the desired substance administration schedule and concentration of each substance to be delivered per electrical stimulation of the polymer film, defined regions of the films loaded with specific substances are removed and assembled into the substance delivery sheet. This sheet may have a checkerboard pattern of components each with a similar area. Alternatively, the sheet has components with different areas and shapes, each electrically conductive and insulated from each other. In this manner, a multi-substance delivery sheet is constructed which releases a predetermined number and amount of substances after stimulation of each component polymer film with an electrical pulse.

As described above, multiple substance delivery sheets or assemblies may be prepared in many configurations. In another embodiment of a substance delivery system, annuli of one or multiple types of substance delivery polymer films are assembled into a series of electrically insulated concentric rings such that exhaustion of substance release from one ring initiates the deterioration of the insulating zone thereby electrically activating substance release from the next ring.

In one embodiment of this invention, a multi-substance delivery sheet is designed for cell culture. Such a sheet incorporates component substance delivery polymer films which are loaded individually with an antibiotic, a growth factor, an amino acid, an enzyme, an enzyme inhibitor, serum components, hormones, immunomodulators, neurotransmitters and possibly other substances. In one embodiment the individual films are not insulated form each other but are electrically connected to each other so that changing the voltage across the film causes release of multiple substances. An example of a specific embodiment of the substances in a multi-substance delivery sheet is the following; streptomycin, penicillin, colony stimulating factor, fibroblast growth factor, L-tryptophan, L-glutamine, aspartate aminotransferase, bacitracin, fetal calf serum proteins, growth hormone, insulin, interleukin, and dopamine. These multisubstance delivery sheets are constructed to fit in a multi-well culture plate or in a culture flask. These plates and flasks are electrically conductive or possess terminals for contacting the films and conducting the electrical signals. Electrical stimulation of the sheet causes the release of all the substances on the multi-substance delivery sheet and thereby provides access of the cultured cells to the substances. This system obviates the need for frequent and multiple additions of substances to the multi-well plates and culture flasks, reduces pipetting steps and their inherent error and variation in substance addition, and reduces the risk of contamination.

Other embodiments of the multi-substance delivery sheet include implants into patients for the administration of substances including therapeutic substances. For example, a sheet designed to promote superficial wound healing might be include substances which inhibit infection, promote skin growth, and promote vascularization. This sheet might be designed to drape over the wound.

In other cases, multi-substance delivery films are designed to promote internal healing following surgery and decrease the incidence of adhesions, infections and possible immune rejection.

Other implantable multi-substance delivery sheets for use in acquired immunodeficiency syndrome (AIDS) might be loaded with t-lymphocytes, immunostimulatory substances, protease inhibitors and antibiotics specific for whatever opportunistic infections might affect a patient with AIDS.

EXAMPLE XVII
Selection and Rapid Growth of a Homogeneous Population of Stem Cells from a Mixed Population of KG1A and Daudi Cells In a 10 ml beaker, 6.0 ml of 0.1 M sodium phosphate buffer at a pH of 7.0 was added to 0.8 ml pyrrole. 0.35 ml of either solution 1, solution 2, or solution 3 described in Example XXI was added. A 1 cm$^2$ square of indium tin oxide glass connected to an anode and a cathode was placed in the solution. The indium tin oxide glass acts as a support for growth of the polymer membrane.

The synthesis of the biologically-active polymer membrane was initiated by applying the following sequence of voltages to the glass: 1.0 V for 1 minute; 1.6 V for 1 minute; 4.0 V for 10 seconds; followed by 2.0 V. Next 30 μl of CD 34 monoclonal antibodies (1 mg protein/ml) was added and the synthesis continued for 2 minutes at 2 V. The glass and attached biologically-active polymer membrane were rinsed with Hank's medium and then stored in Hank's medium in the refrigerator.

The biologically-active polymer membrane was placed in a Petri dish and KG1a stem cells 1×10$^5$ (from ATCC) were added at 4° C. in Hank's medium together with Daudi cells 1×10$^5$ (obtained from ATCC). The Petri dish was maintained at room temperature (approximately 22–24° C.). Approximately 40 minutes later, signs of cell growth were evident. Cells were extending and dividing. The cells were maintained at 37° C. in 5% CO$_2$. About 2 hours later the Petri dish was removed and the cells examined. The number of cells was about twice that observed 40 minutes after the previous examination of the cells. The cells grown on the biologically-active polymer membrane produced in this Example were very homogeneous in appearance when examined at 1 and 5 days after the start of the culture.

EXAMPLE XVIII
Selection, Differentiation and Growth of Heterogeneous Cells Derived from a Mixed Population of KG1A and Daudi Cells In a 10 ml beaker, 6.0 ml of 0.1 M sodium phosphate buffer at a pH of 7.0 was added to 0.8 ml pyrrole. 0.35 ml of either solution 1, solution 2, or solution 3 described in Example XXI was added. A 1 cm$^2$ square of indium tin oxide glass connected to an anode and a cathode was placed in the solution. The indium tin oxide glass acts as a support for growth of the polymer membrane.

Next 30 μl of CD34 antibodies monoclonal antibodies (1 mg protein/ml) were added (final dilution about 1:238). The synthesis of the membrane was initiated by applying the following sequence of voltages to the glass: 13.0 V momentarily; and 2.98 V for 1 minute. The glass and attached polymer membrane were rinsed with Hank's medium and then stored in Hank's medium in the refrigerator.

The biologically-active polymer membrane was placed in a Petri dish and KG1a stem cells 1×10$^5$ (from ATCC) were added at 4° C. in Hank's medium together with Daudi cells 1×10$^5$ (obtained from ATCC). The Petri dish was maintained at room temperature (approximately 22–24° C.) for 40 minutes. The cells were maintained at 37° C. in 5% CO$_2$. About 2 hours later the Petri dish was removed and the cells examined. The number of cells was about twice that observed 40 minutes after the previous examination of the cells. The cells grown on the biologically-active polymer membrane produced in this Example displayed a variety of cell types when examined at 1 and 5 days after the start of the culture.

EXAMPLE XIX
Selection and Rapid Growth of a Homogeneous Population of Cells from a Mixed Population of KG1A and Daudi Cells In a 10 ml beaker, 6.0 ml of 0.1 M sodium phosphate buffer at a pH of 7.0 was added to 0.8 ml pyrrole. 0.35 ml of either solution 1, solution 2, or solution 3 described in Example XXI was added. A 1 cm$^2$ square of indium tin oxide glass connected to an anode and a cathode was placed in the solution. The indium tin oxide glass acts as a support for growth of the polymer membrane.

Next 30 μl of CD34 antibodies monoclonal antibodies (1 mg protein/ml) were added (final dilution about 1:238) synthesis of the biologically-active polymer membrane was initiated by applying the following sequence of voltages to the glass: 2.98 V for 1 minute; 0 V momentarily; and then 4.0 V for 1 minute. The glass and attached biologically-active polymer membrane were rinsed with Hank's medium and then stored in Hank's medium in the refrigerator.

The biologically-active polymer membrane was placed in a Petri dish and KG1a stem cells 1×10$^5$ (from ATCC) were added at 4° C. in Hank's medium together with Daudi cells 1×10$^5$ (obtained from ATCC). The Petri dish was maintained at room temperature (approximately 22–24° C.) for 40 minutes. The cells were maintained at 37° C. in 5% CO$_2$. About 2 hours later the Petri dish was removed and the cells examined. The number of cells was about twice that observed 40 minutes after the previous examination of the cells. The cells grown on the biologically-active polymer membrane produced in this Example were fairly consistent in appearance and displayed primarily a single cell type when examined at 1 and 5 days after the start of the culture.

EXAMPLE XX
Selection, Differentiation and Growth of Cells Derived from a Mixed Population of KG1A and Daudi Cells into Sheets and Layers of Cells In a 10 ml beaker, 6.0 ml of 0.1 M sodium phosphate buffer at a pH of 7.0 was added to 0.8 ml pyrrole. 0.35 ml of either solution 1, solution 2, or solution 3 described in Example XXI was added. A 1 cm$^2$ square of indium tin oxide glass connected to an anode and a cathode was placed in the solution. The indium tin oxide glass acts as a support for growth of the biologically-active polymer membrane.

Next 30 μl CD34 antibodies monoclonal antibodies (1 mg protein/ml) were added (final dilution about 1:238). The synthesis of the biologically-active polymer membrane was initiated by applying the following sequence of voltages to the glass: 4.0 V for 2 minutes; and then 1.8 V for 10 minutes. The glass and attached biologically-active polymer membrane were rinsed with Hank's medium and then stored in Hank's medium in the refrigerator.

The biologically-active polymer membrane was placed in a Petri dish and KG1a stem cells 1×10$^5$ (from ATCC) were added at 4° C. in Hank's medium together with Daudi cells 1×10$^5$ (obtained from ATCC). The Petri dish was maintained at room temperature (approximately 22–24° C.) for 40 minutes. The cells were maintained at 37° C. in 5% CO$_2$. About 2 hours later the Petri dish was removed and the cells examined. The number of cells was about twice that observed 40 minutes after the previous examination of the cells. The cells grown on the biologically-active polymer membrane produced in this Example were organized in sheets and also multiple layers when examined at 1 and 5 days after the start of the culture.

EXAMPLE XXI
Solution 1 is comprised of 1.3 g of p-toluene sulfonic acid (sodium salt) in 20 ml of H$_2$O. Solution 2 is comprised of 0.75 g naphthalene 2-sulfonic acid in 25 ml of acetonitrile and 5 ml of $H_2O$. Solution 3 is comprised of a equal parts of Solutions 1 and 2. Solutions 1, 2, or 3 may be used in Examples XVII through XX described above.

EXAMPLE XXII
Electrically-induced Differentiation of Stem Cells Isolated from a Mixed Population of KG1A and Daudi Cells The same method as in Example XVII was used. After allowing stem cells to incubate for 40 minutes at room temperature, the biologically-active polymer membrane was activated electrically by applying 0.5 V across the membrane for minutes. The cells were then placed in a 5% $CO_2$ incubator at 32° C. for 2 hours. Examination of the cells revealed many different types of cells, unlike that of Example XVII.

EXAMPLE XXIII
Electrically-induced and Reversible Growth of Stem Cells Isolated from a Mixed Population of KG1A and Daudi Cells The same procedure was followed as in Example XXII, but the voltage applied was 0.8 V. Noticeable changes were evident under the microscope in the cell differentiation and growth behavior while applying the voltage. For example, immediately after applying the potential, significant cell extensions were noticed. When the voltage was lowered (or reversed) an immediate retraction to normal spherical shapes resulted.

It should be understood, of course, that the foregoing relates only to preferred embodiments of the present invention and that numerous modifications or alterations may be made therein without departing from the spirit and the scope of the invention.

What is claimed is:

1. A polymer composition comprising a polymer and an antibody, wherein the polymer is selected from the group consisting of polymers of pyrrole, thiophene, aniline, and combinations thereof, said polymer composition being adapted to bind specifically to an analyte and to release the analyte, and said polymer composition is prepared by a process comprising:
   mixing an aqueous solution of acetonitrile and an electrolyte to make a mixture wherein the electrolyte is p-toluene sulfonic acid, naphthalene sulfonic acid, tetraacetyl ammonium toluene sulfonate, or a combination of p-toluene sulfonic acid and naphthalene sulfonic acid;
   increasing pH of the mixture through addition of base to the mixture;
   inserting an electrode into the mixture;
   adding one or more monomers to the mixture, wherein the one or more monomers is pyrrole, thiophene, analine, or a combination thereof;
   adding an antibody to the mixture, wherein the antibody is capable of binding to the analyte;
   applying a voltage to the electrode, wherein the voltage produces a direct current; and,
   altering the voltage.

2. The polymer composition of claim 1, further adapted to measure an amount of an analyte that binds specifically to the polymer composition.

3. The polymer composition of claim 1, wherein the analyte is a molecule, macromolecule, organelle, cell, virus, bacterium, fungus, protozoan, or parasite.

4. The polymer composition of claim 3, wherein the analyte is a cell.

5. The polymer composition of claim 4, wherein the cell is derived from ectoderm, mesoderm, or endoderm.

6. The polymer composition of claim 4, wherein the cell is a stem cell.

7. The polymer composition of claim 6, wherein the stem cell is a lympho-hematopoietic stem cell, bone marrow stem cell, mesenchymal cell, neuroepithelial cell, neuroblast, glioblast, fibroblast, osteoblast, germ cell, myoblast, or an umbilical cord blood stem cell.

8. A method of isolating an analyte comprising:
   contacting the polymer composition of claim 1 with a first solution containing the analyte;
   allowing the analyte to bind to the polymer composition;
   washing the polymer composition with a second solution not containing the analyte; and
   applying a signal to the polymer composition, wherein the signal is sufficient to release the analyte from the polymer composition, and the signal is an electric current, a change in voltage, an alteration in polarity, or a change in ionic strength of the second solution.

9. The method of claim 8, wherein the analyte is a molecule, macromolecule, organelle, cell, virus, bacterium, fungus, protozoan, or parasite.

10. The method of claim 8, wherein the analyte is a cell.

11. The method of claim 10, wherein the cell is derived from ectoderm, mesoderm, or endoderm.

12. The method of claim 10, wherein the cell is a stem cell.

13. The method of claim 12, wherein the stem cell is a lympho-hematopoietic stem cell, bone marrow stem cell, mesenchymal cell, neuroepithelial cell, neuroblast, glioblast, fibroblast, osteoblast, germ cell, myoblast, or an umbilical cord blood stem cell.

14. A polymer composition comprising polymers of pyrrole, thiophene, aniline, or combinations thereof, and an antibody, wherein the polymer composition is formed in the presence of acetonitrile and an electrolyte selected from the group consisting of p-toluene sulfonic acid, naphthalene sulfonic acid, a combination of p-toluene sulfonic acid and naphthalene sulfonic acid, and tetraacetyl ammonium toluene sulfonate, wherein the antibody is capable of specifically binding to an analyte, and wherein the polymer composition is adapted to bind specifically to the analyte and to release the analyte upon application of a signal to the polymer composition, wherein the signal is sufficient to release the analyte from the polymer composition and the signal is an electric current, a change in voltage, an alteration in polarity, or a change in ionic strength of a solution surrounding the polymer composition.

15. The polymer composition of claim 3, wherein the analyte is a virus.

16. The polymer composition of claim 3, wherein the analyte is a bacterium.

17. The method of claim 8, wherein the analyte is a virus.

18. The method of claim 8, wherein the analyte is a bacterium.

19. The polymer composition of claim 14, wherein the antibody recognizes the analyte, and the analyte is a molecule, macromolecule, organelle, cell, virus, bacterium, fungus, protozoan, or parasite.

20. A method of measuring an analyte comprising:
   placing an electric current across the polymer composition of claim 1;
   measuring an initial voltage of the polymer composition;
   contacting the polymer composition with a solution containing the analyte;

allowing the analyte to bind to the polymer composition;

measuring a final voltage of the polymer composition;

calculating a voltage differential by comparing the initial voltage and the final voltage; and comparing the voltage differential to other voltage differentials produced by binding standard concentrations of the analyte to the polymer composition.

21. The method of claim 20, wherein the analyte is a molecule, macromolecule, organelle, cell, virus, bacterium, fungus, protozoan, or parasite.

22. The method of claim 20, further comprising measuring more than one analyte, comprising:

using more than one polymer composition of claim 1, wherein each polymer composition contains an antibody which binds specifically to an analyte, measuring an initial voltage of each polymer composition;

contacting the polymer compositions with a solution containing more than one analyte;

allowing the analytes to bind to the polymer compositions;

measuring a final voltage of each polymer composition;

calculating a voltage differential for each polymer composition by comparing the initial voltage and the final voltage of each polymer composition; and comparing the voltage differential for each polymer composition to other voltage differentials produced by binding standard concentrations of each analyte specifically bound to each polymer composition.

23. The method of claim 22, wherein the analytes are molecules, macromolecules, organelles, cells, viruses, bacteria, fungi, protozoa, parasites, or combinations thereof.

* * * * *